United States Patent [19]

Turner et al.

[11] 4,002,739
[45] Jan. 11, 1977

[54] SOLUBLE COLLAGEN

[75] Inventors: James E. Turner, Madison; James R. Butler, Parsippany, both of N.J.

[73] Assignee: Warner-Lambert Company, Morris Plains, N.J.

[22] Filed: Feb. 18, 1975

[21] Appl. No.: 550,790

[52] U.S. Cl. ............................................. 424/177
[51] Int. Cl.$^2$ .................... A61K 37/00; C08H 1/00
[58] Field of Search .................. 424/177; 426/641

[56] References Cited
UNITED STATES PATENTS

| | | | |
|---|---|---|---|
| 3,580,725 | 5/1971 | Kuster | 426/641 |
| 3,803,299 | 4/1974 | Nouel | 424/177 |

OTHER PUBLICATIONS

Podhorschi: Chem. Abstr. 71:126,031v (1969).
Japan Leather: Chem. Abstr. 67:118,126g (1967).

*Primary Examiner*—Lewis Gotts
*Assistant Examiner*—Reginald J. Suyat
*Attorney, Agent, or Firm*—Albert H. Graddis; Frank S. Chow; George M. Yahwak

[57] ABSTRACT

A soluble lyophilized collagen preparation is disclosed which is capable of reproducible aggregating platelets.

13 Claims, No Drawings

SOLUBLE COLLAGEN

The primary hemostatic event in the body is the adsorption of platelets to subendothelial collagen exposed by a lesion in a blood vessel. This is followed immediately by a wholesale aggregation of platelets around the lesion resulting in a platelet plug which prevents the leakage of blood and provides a matrix for clot formation.

Several pathological conditions are related to the aggregation of blood platelets. A decrease in the ability of platelets to aggregate, for example, can lead to clotting and bleeding disorders. On the other hand, an increased tendancy for platelets to aggregate can initiate unwanted thrombus formation and could possibly result in myocardial infarction or other intravascular clotting problems.

In order to diagnose a particular bleeding episode or to assess the probability of further bleeding or clotting problems, it is necessary to evaluate the ability of a patient's platelets to aggregate. This is usually accomplished in vitro by determining the degree of platelet aggregation caused by various aggregating agents such as adenosine diphosphate, epinephrine or collagen. This determination usually is carried out with a platelet aggregometer. This instrument measures the amount of light passing through a sample of platelet rich plasma undergoing aggregation.

Collagen is usually the agent of choice in determining aggregation since it is involved in the primary hemostatic event in vivo. However, since suitable collagen preparations are not commercially available, only a few clinical laboratories make and use their own collagen preparations. These preparations are usually suspensions rather than true solutions and, consequently, exhibit poor reproducibility from preparation to preparation. In addition, they lose their platelet activity when dried and, therefore, must be stored as a suspension at 4° C. As a result, their stability is measured in days.

We have now discovered an improved collagen preparation which eliminates most of the problems and difficulties incurred with insoluble collagen suspensions.

Accordingly, it is the object of this invention to describe a method of obtaining soluble collagen capable of aggregating platelets from insoluble collagen.

It is a further object of this invention to describe a procedure for preparing a stable, lyophilized form of soluble collagen that retains its platelet agglutinating activity following redissolution in water.

The following example is given to allow for a better understanding of the invention:

EXAMPLE 1

Method of Preparation

I. Acid-soluble collagen suspension

Achilles tendon collagen (25 mg) is allowed to hydrate overnight at 4° C. in 25 ml of 0.522M acetic acid. The mixture is transferred to a 50 ml homogenizing jar and homogenized with a Virtis Super 30 Homogenizer at a setting of 80 for 30 minutes at 5–8° C. The resulting suspension is centrifuged at 2500 × g for 15 minutes at room temperature. If no button is observed in the bottom of the centrifuge tube, the solution is stirred slowly for 15 minutes and filtered through a plug of glass wool; if a button is observed the solution is discarded.

II. Dilution of collagen solution

The filtered suspension containing 1 mg collagen/ml is diluted with 0.2% aqueous solution of bovine serum albumin to obtain 8µg collagen/ml.

III. Lyophilization of collagen solution

One ml aliquots of the collagen solution are lyophilized for 30 hours in suitable vials. Following lyophilization, the vials are capped and stored at 4° C.

IV. Reconstitution of lyophilized collagen

One ml of water is added to the vial and it is allowed to stand at room temperature for 10 minutes. The contents are then mixed for 10 seconds on a vortex mixer at medium speed. The reconstituted solution should be pH 3.0 to 4.5, preferably pH 3.8.

EXAMPLE 2

Method for preparing buffered, soluble collagen

I. Acid-soluble collagen suspension

"The same description as in Example 1, Step I."

II. Preparation of 0.05M glycine-HCl buffer

Glycine (3.7535 g) and 2.0 g bovine serum albumin (BSA) are dissolved in 900 ml distilled water. The solution is adjusted with 0.1N HCl to pH 3.0 to 4.5, preferably pH 3.8, and then brought to a final volume of 1000 ml with water. The pH is readjusted with additional HCl if necessary.

III. Dilution of collagen solution

The filtered solution containing 1.0 mg collagen/ml is diluted with the glycine buffer — BSA solution to obtain the desired collagen concentration, preferably 8µg/ml.

IV. Lyophilization of collagen solution

"The same description as in Example 1, Step III."

V. Reconstitution of lyophilized collagen

"The same description as in Example 1, Step IV."

An acid solution preparation of collagen (2.5 mg/ml) was lyophilized with and without 7% bovine serum albumin (BSA) following the protocol of Example 1, Part I. Only the lyophilized preparation containing the BSA could be redissolved with complete aggregation of platelets being observed. However, these were small aggregates resulting in small oscillations in the aggregometer tracings, while a desirable property of a collagen preparation is the ability to produce large platelet aggregates and large aggregometer oscillations as depicted in the graph below. This data suggests that the 7% BSA concentration exhibited a small inhibitory affect on platelet aggregation.

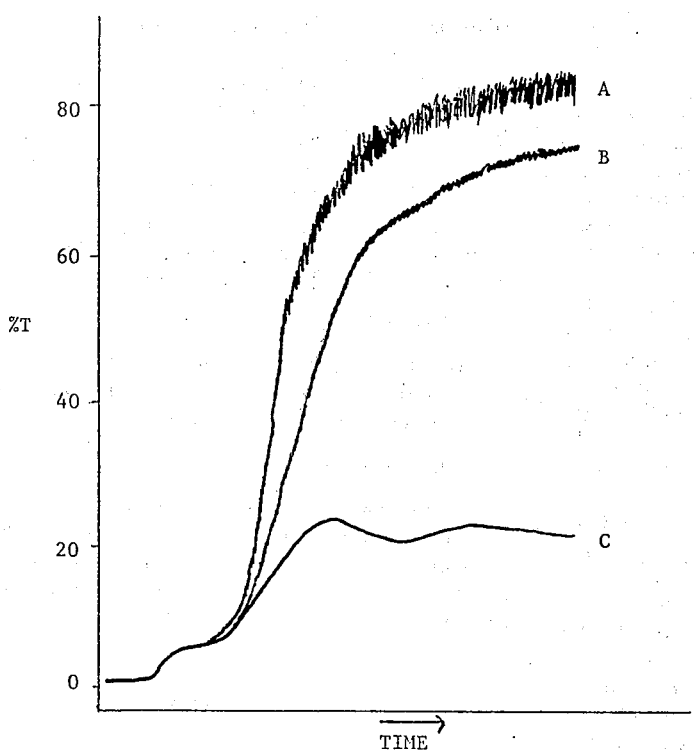

Figure 1: Collagen mediated platelet aggregation profiles of the following:
A - normal platelet aggregation with large oscillations
B - normal platelet aggregation with small oscillations
C - aspirin inhibition of platelet aggregation Lyophilized preparations containing 1 to 5% BSA were reconstituted with water or 0.522M acetic acid. The preparations reconstituted with water aggregated the platelets completely, but the tracing oscillations again were small. This indicated that a concentration of BSA as low as 1% still had a slight inhibitory affect on platelet aggregation. Those preparations reconstituted with acetic acid did not aggregate platelets indicating an additional inhibition caused by acetic acid. Fortunately, the lyophilization in addition to drying the preparation, also removed some of the acetic acid and lowered the acidity of the samples reconstituted with water from pH 2 to pH 4. This resulted in a more active product. The unexpected reduction of acidity by lyophilization rather than by neutralization with alkali also prevented an increase in ionic strength and thereby insured complete redissolution of the collagen in water.

Further collagen preparations were lyophilized with concentrations of BSA ranging from 0.05 to 1.0%. The results of the degree of platelet aggregation which is directly related to percent light transmission are found in Table I.

Table I indicates that aggregation is not significantly affected by a BSA concentration up to 1%. However, complete solubility of collagen was obtained with as little as 0.2% BSA and therefore this concentration was used for the subsequent studies.

In order to determine the optimal quantity of collagen required for platelet aggregation, various quantities of a reconstituted collagen preparation containing 0.2% BSA were added to human platelet rich plasma. It was observed that 10 $\mu$l, 20 $\mu$l, and 50 $\mu$l of a 2.5 mg/ml suspension produced complete aggregation. Therefore, more dilute solutions of collagen were prepared, lyophilized, and reconstituted in water. The degree of aggregation produced by 50 $\mu$l of each preparation is also shown in Table I. In addition, further dilutions of a reconstituted collagen preparation containing 0.125 mg/ml were made with 1% BSA and are also included in Table I.

TABLE I

Degree of Platelet Aggregation Produced by Seven Concentrations of Collagen

| | | Collagen (mg/ml) | BSA (percent) | Platelet Aggregation (% transmission) |
|---|---|---|---|---|
| A | | 0–25 | 0–05 | did not reconstitute |
| B | | 0–25 | 0–10 | did not reconstitute |
| C | | 0–25 | 0–20 | 87 |
| D | | 0–25 | 1–0 | 84 |
| E | | 0–125 | 0–05 | 85 |
| F | | 0–125 | 0–10 | 77 |
| G | | 0–125 | 0–20 | 76 |
| H | (1) | 0–125 | 1–0 | 84 |
| | (2) | 0–0625 | 1–0 | 82 |
| | (3) | 0–0313 | 1–0 | 78 |
| | (4) | 0–0156 | 1–0 | 76 |
| | (5) | 0–008 | 1–0 | 64 |
| | (6) | 0–005 | 1–0 | 17 |
| | (7) | 0–004 | 1–0 | 21 |

Complete aggregation was obtained with either the 0.250 mg/ml or the 0.125 mg/ml preparation. When the six serial dilutions of the 0.125 mg/ml solution in 1% BSA were assayed for platelet aggregating activity, a concentration of 8 $\mu$g/ml of collagen was found to produce an optimal but not maximal level of platelet aggregation. Under these experimental conditions, the optimal level of platelet aggregation exhibited by normal individuals is approximately 60% transmission which allows detection of large deviations above and below the normal value.

Stability studies indicated that soluble collagen prepared according to this invention was stable for at least 8 months at room temperature; for up to 2 weeks at 45° C; and for at least 9 months at 4° C. The stability after reconstitution was 3 hours at room temperature.

Aspirin and certain other drugs are known to inhibit platelet aggregation as depicted in the graph above. Therefore, an experiment was performed to determine whether the 8 µg collagen/ml preparation could distinguish between normal platelet aggregation and abnormal platelets. Platelet rich plasmas were obtained from three volunteers before and after ingestion of aspirin, and then assayed for platelet aggregation.

Table II shows that the soluble collagen preparation was capable of detecting in vivo aspirin inhibition of platelet aggregation in all of the samples.

TABLE II

| In Vivo Effect of Aspirin on Platelet Aggregation PERCENT TRANSMISSION | | |
|---|---|---|
| DONOR No. | Before Aspirin Ingestion | After Aspirin Ingestion |
| 1 | 62 | 24 |
| 2 | 55 | 13 |
| 3 | 62 | 20 |

We claim:

1. A composition of matter for use in measuring blood platelet aggregation comprising a solution of acidic collagen and bovine serum albumin said composition having a pH of between about 3.0 to about 4.5.

2. A composition of matter according to claim 1 wherein the bovine serum albumin is in a sufficient amount to obtain a concentration of about 5 to about 1000 µg of collagen per milliliter.

3. A composition of matter according to claim 2 comprising acidic collagen and sufficient bovine serum albumin added thereto to obtain a concentration of about 5 to about 10 µg of collagen per milliliter.

4. The composition of claim 3 wherein the acidic collagen comprises acetic acid and collagen.

5. The composition of claim 3 which is lyophilized.

6. The composition of claim 3 wherein the concentration of collagen is about 8 µg per milliliter.

7. A method of preparing a collagen solution comprising the steps of:
Hydrating an amount of collagen at 4° C in an amount of acetic acid to obtain a collagen solution having a pH of between about 3.0 to about 4.5 and one which is free of particulate matter which is capable of being centrifuged out of the solution when the solution is centrifuged at 2500 × G for a period of fifteen minutes;
Homogenizing the material so obtained to form a uniform solution; and
Diluting the homogenized material with a sufficient amount of bovine serum albumin to obtain a collagen concentration of about 5 to about 1000 µg per ml of diluted solution.

8. The method of claim 7 which further comprises lyophilizing the diluted material.

9. The method of claim 7 wherein the diluent is a 0.2% aqueous solution of bovine serum albumin.

10. The method of claim 7 wherein the concentration is adjusted to about 5 to about 10 µg of collagen per ml of diluted solution.

11. The method of claim 10 wherein the concentration is adjusted to 8 µg per ml. of diluted solution.

12. The method of claim 7 wherein the acid is about 0.522M acetic acid.

13. The method of claim 7 wherein the material is homogenized at 5°–8° C.

* * * * *